US008019857B2

(12) United States Patent
Nguyen

(10) Patent No.: US 8,019,857 B2
(45) Date of Patent: Sep. 13, 2011

(54) FLEXIBLE SYSTEM HEALTH AND REMEDIATION AGENT

(75) Inventor: Man Nguyen, Vancouver, WA (US)

(73) Assignee: Microsoft Corporation, Redmond, WA (US)

(*) Notice: Subject to any disclaimer, the term of this patent is extended or adjusted under 35 U.S.C. 154(b) by 141 days.

(21) Appl. No.: 12/207,503

(22) Filed: Sep. 10, 2008

(65) Prior Publication Data

US 2010/0063855 A1 Mar. 11, 2010

(51) Int. Cl.
*G06F 15/173* (2006.01)
(52) U.S. Cl. .......................... 709/224; 706/47
(58) Field of Classification Search .................. 709/223, 709/224, 202, 203; 726/1, 3, 6, 14, 22–26; 717/100, 120, 124, 127, 128; 706/47
See application file for complete search history.

(56) References Cited

U.S. PATENT DOCUMENTS

| 2005/0187963 | A1* | 8/2005 | Markin .......................... 707/102 |
| 2005/0267954 | A1 | 12/2005 | Lewis et al. |
| 2006/0085850 | A1 | 4/2006 | Mayfield et al. |
| 2006/0095961 | A1 | 5/2006 | Govindarajan et al. |
| 2006/0200803 | A1* | 9/2006 | Neumann et al. ............. 717/120 |
| 2007/0118567 | A1 | 5/2007 | Isokawa |
| 2007/0130624 | A1 | 6/2007 | Shah et al. |
| 2007/0136297 | A1 | 6/2007 | Choe |
| 2007/0143827 | A1* | 6/2007 | Nicodemus et al. ............... 726/2 |
| 2007/0198525 | A1 | 8/2007 | Chatterjee et al. |
| 2007/0234040 | A1 | 10/2007 | Hurst et al. |
| 2008/0301765 | A1* | 12/2008 | Nicol et al. ...................... 726/1 |
| 2009/0049518 | A1* | 2/2009 | Roman et al. ...................... 726/1 |
| 2009/0205011 | A1* | 8/2009 | Jain et al. ........................... 726/1 |
| 2009/0205012 | A1* | 8/2009 | Jain et al. ........................... 726/1 |

OTHER PUBLICATIONS

"What is Microsoft TCM Spider?", Retrieved at<< http://msdn.microsoft.com/en-us/security/cc299442.aspx >>, May 30, 2008, pp. 3.
Brien M. Posey,"Windows Network Access Protection (NAP) Simplifies Quarantine Mode", Retrieved at<< http://articles.techrepublic.com.com/5100-10878_11-5298997.html >>, Aug. 11, 2004, pp. 5.
Michael Cherry,"Windows Server 2008 Controls Network Access", Retrieved at<< http://www.directionsonmicrosoft.com/sample/DOMIS/update/2007/12dec/1207ws2cna.htm >>, Nov. 12, 2007, pp. 3.
Peter Y.Moss,"Network Access Protection (NAP) in Windows Vista", Retrieved at<< http://e-articles.info/e/a/title/Network-Access-Protection-(NAP)-in-Windows-Vista/ >>, Mar. 2007, pp. 3.
"Implementing Quarantine Services with Microsoft Virtual Private Network Planning Guide", Retrieved at<< http://www.microsoft.com/technet/security/prodtech/windowsserver2003/quarantineservices/vppgch02.mspx >>, May 30, 2008, pp. 5.

* cited by examiner

*Primary Examiner* — Frantz B Jean
(74) *Attorney, Agent, or Firm* — Boswell IP Law; J. Mason Boswell

(57) ABSTRACT

A flexible compliance system is described herein that provides a deployable system health agent and automated remediation of computer system compliance failures based on configurable compliance rules. An administrator defines rules that represent compliance elements that the flexible compliance system will enforce. The flexible compliance system reads the rules defined by the administrator like a flexible set of conditions to check, and checks client computer systems based on the rules. The flexible compliance system generates a statement of health that indicates whether the computer system satisfies or violates each rule. In response to the statement of health, the flexible compliance system may take various actions with respect to a computer system in violation of a rule, including attempting to resolve the violation or quarantining the computer system to avoid interaction with other computer systems.

20 Claims, 4 Drawing Sheets

FLEXIBLE SYSTEM HEALTH AND REMEDIATION AGENT

BACKGROUND

Organizations today are subject to a variety of regulations related to computer systems within the organization. Often, organizations undergo regular auditing to verify compliance with these regulations. General guidelines have been established for systems within an organization. For example, the Control Objectives for Information and related Technology (COBIT) is a set of best practices (i.e., a framework) for information technology (IT) management created by the Information Systems Audit and Control Association (ISACA) and the IT Governance Institute (ITGI) in 1992. COBIT provides managers, auditors, and IT users with a set of generally accepted measures, indicators, processes, and best practices to assist them in improving the benefits derived through the use of information technology and developing appropriate IT governance and control in an organization. For example, some practices specify the applications that are allowed to run or that each computer system has up to date antivirus software. Other regulations govern specific industries. For example, the Health Insurance Portability and Accountability Act (HIPAA) enacted by the U.S. Congress in 1996 contains provisions that require health care providers to protect the privacy of patient information. These provisions extend to data stored on a health care provider's computer systems, and organizations often seek to verify the organization's compliance with such regulations.

Non-compliant systems are those computing systems within an organization that do not comply with one or more regulations placed in effect by the organization. There are two priorities that an organization typically has with respect to non-compliant computer systems. First, the organization wants to isolate non-compliant systems from compliant systems, to avoid spreading a problem or avoid unauthorized access to sensitive organizational data. For example, if a non-compliant computer system has a computer virus, the organization wants to avoid that virus spreading to other computer systems within the organization. Second, the organization wants to bring the non-compliant computer system back into compliance. This ensures that the user of the non-compliant computer system receives the level of service from the organization's IT resources that the user expects. For example, the user may expect to be able to access a corporate email server to check email, but for the security of other systems may be prevented from doing so if there is a problem with compliance.

Most compliance applications today focus on auditing and detection of violations of the types of regulations or best practices noted above. These applications may routinely scan an organization's network to evaluate each computer system's compliance with a best practice. The applications often generate a report that IT personnel review and act upon. For example, the IT personnel may communicate with a user of a non-compliant computer system or block the non-compliant computer system from accessing certain resources (e.g., a corporate network). Existing systems provide a lot of information, but generate a correspondingly high burden on IT personnel that later consume the information and act upon it.

SUMMARY

A flexible compliance system is described herein that provides a deployable system health agent and automated remediation of computer system compliance failures based on configurable compliance rules. An administrator defines one or more rules that represent compliance elements that the flexible compliance system will enforce. When a specified event occurs, the system checks the compliance state (i.e., health) of a particular computer system. The flexible compliance system reads the rules defined by the administrator like a flexible set of conditions to check, and correlates the outcome of the conditions to the rules. The flexible compliance system generates a statement of health that indicates whether the computer system satisfies or violates each rule. In response to the statement of health, the flexible compliance system may take various actions with respect to a computer system in violation of a rule, including attempting to resolve the violation or quarantining the computer system to avoid interaction with other computer systems. Administrators can use the flexible compliance system to define these and many other types of actions to remediate non-compliant computer systems and protect the health of the organization's network resources.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

DETAILED DESCRIPTION

Figure 1:
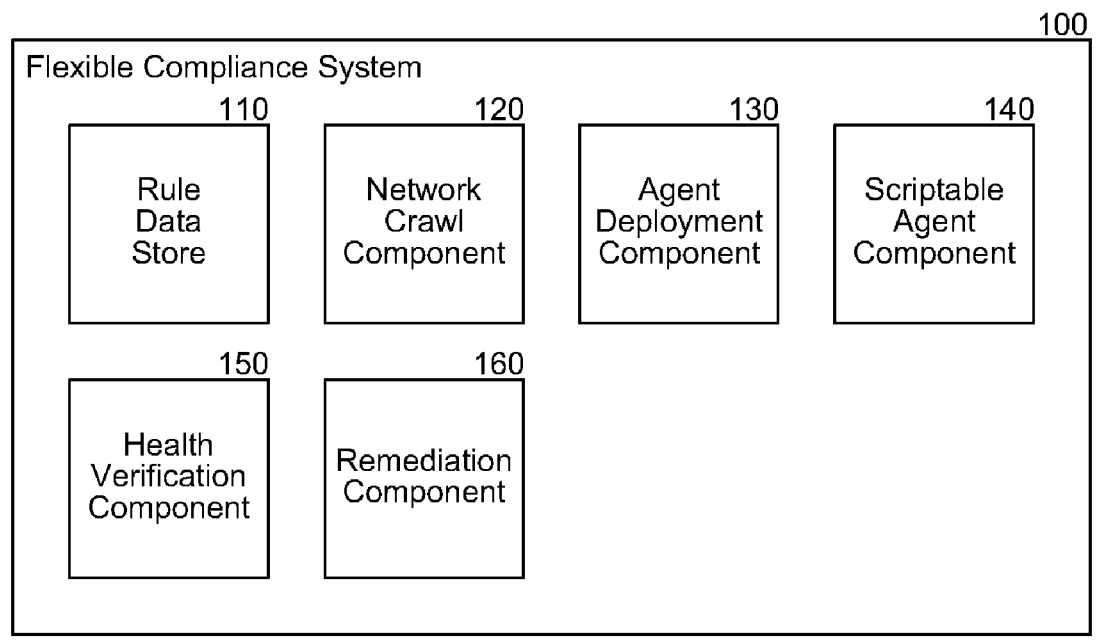
FIG. 1 is a block diagram that illustrates components of the flexible compliance system, in one embodiment.

A flexible compliance system is described herein that provides a deployable system health agent and automated remediation of computer system compliance failures based on configurable compliance rules. Unlike previous systems, the flexible compliance system integrates remediation of a compliance problem in an automated process that often does not involve the manual intervention of IT personnel. In addition, the system is flexible enough to allow an organization to define its own set of conditions for which the system checks and to define associated remediation steps that the system performs when the conditions are met. Thus, IT personnel are free to spend time on other tasks, such as improving the organization's policies or services.

In some embodiments, an administrator begins by defining one or more rules that represent compliance elements that the flexible compliance system will enforce. A rule can include a descriptive title (e.g., the COBIT section from which the rule is derived), one or more conditions that determine whether a computer system satisfies or violates the rule, and one or more remediation actions to take if a computer system violates the rule. For example, a rule condition may specify a particular value of a registry key (e.g., service pack version, virus signature, and so forth) that the system will look for to determine if the rule is satisfied. For example, a rule condition may determine whether an antivirus service is set to run automatically at startup for a particular computer system by looking at the service startup value (e.g., for Windows "HKEY_LOCAL_MACHINE\ SYSTEM\ CurrentControlSet\ Services\ <service name>\ Start"). At some point, a machine check event occurs that causes the system to check the compliance state (i.e., health) of a particular computer system. For example, a machine check event may be a logon of the computer system to a corporate network, the expiration of a timeout, the installation of a new application on the computer system, and so on.

When the machine check event occurs, the flexible compliance system surveys the compliance of the computer system. For example, the flexible compliance system may crawl the hard drive, registry, or other data store of the computer system to evaluate whether each rule defined by the administrator is satisfied. The flexible compliance system may operate as a service on the computer system or may be a downloaded set of instructions (e.g., a logon script or other installable module) that the flexible compliance system deploys to the computer system. The flexible compliance system reads the rules defined by an administrator like a flexible set of conditions to check (e.g., a script), and correlates the outcome of the conditions to the rules defined by the administrator. The flexible compliance system may then provide a statement of health to a central system (e.g., a compliance server, domain controller, and so forth) that indicates whether the computer system satisfies or violates each rule.

In response to the statement of health or based on predefined actions, the flexible compliance system may take various actions with respect to a computer system in violation of a rule. For example, the agent described herein running on the computer system may prevent the computer system from acquiring a network address (e.g., using DHCP) to prevent the computer system from having full access to the network. For organizations using IPSEC to secure transmitted data, the agent may prevent the computer system from acquiring a certificate used to make an IPSEC connection to certain systems. As another example, the system may block TLS/Certificates in order to prevent wireless (e.g., 802.11) authentication to RADIUS servers. The system may also attempt to resolve the violation. For example, the system may modify a registry key, delete a file (e.g., containing a virus), or uninstall an application to restore the compliance of the computer system.

Administrators can use the flexible compliance system to define these and many other types of actions to remediate non-compliant computer systems and protect the health of the organization's network resources. In addition, just as the flexible compliance system can quarantine a system that is non-compliant, if the remediation actions bring a computer system back into compliance, then the flexible compliance system may bring the computer system out of quarantine (e.g., by allowing the computer system to acquire an IP address, IPSEC certificate, and so on).

FIG. 1 is a block diagram that illustrates components of the flexible compliance system, in one embodiment. The flexible compliance system 100 includes a rule data store 110, a network crawl component 120, an agent deployment component 130, a flexible agent component 140, a health verification component 150, and a remediation component 160. Each of these components is described in further detail herein.

The rule data store 110 contains a set of compliance rules and enforcement actions (collectively "rules" herein) that the flexible compliance system 100 is assigned to carry out for the organization. For example, compliance rules may include particular operating system or application patches that an administrator expects to be installed on each computer system in the organization. Enforcement actions specify the action the system will take if a computer system is out of compliance. For example, if certain patches are missing, an enforcement action may specify that the computer system not be allowed to access the network or another action may download and install the missing patch. The system 100 may provide an application, web page, or other interface for an administrator to define or import compliance rules and enforcement actions that the system 100 then stores in the rule data store 110.

The network crawl component 120 crawls the network (e.g., like a spider application) checking computer systems for compliance. The network crawl component 120 may receive notification of events, such as a computing system logging on to the network, that start a crawl. The network crawl component 120 may periodically re-crawl the network based on events that occur or a specified duration expiring.

The agent deployment component 130 deploys the agent component 140 to applicable computer systems discovered by the network crawl component 120. For example, if a new machine logs onto the network, the agent deployment component 130 may send the agent component 140 to the computing system and request that the computing system execute the agent component 140 and validate the computer system's current level of compliance (i.e., health).

The flexible agent component 140 is an executable module or script that is deployable to various computer systems within an organization or network. The agent component 140 may be lightweight such that the system 100 can deploy it quickly to a computer system, request that the agent component 140 validate the health of the system, and then request that the agent component 140 remove itself from the computer system. One common request of compliance applications is that they produce as little impact or footprint on the systems that they monitor as possible. The agent component 140 allows the system 100 to deploy a small piece of code for a limited purpose that does not stay on the system when the purpose is fulfilled.

The health verification component 150 can be part of the agent component 140 or a separate component. The agent deployment component 130 may provide the health verification component 150 with rules from the rule data store 110 that the health verification component 150 is expected to validate against a computer system. The health verification component 150 compares the computer system to each compliance rule to determine whether the computer system satisfies the compliance rule. The compliance rule may specify particular conditions to check. For example, the compliance rule may specify a registry key value, file version, or other computer system attribute that the health verification component 150 detects to determine if the rule is satisfied. The health verification component may provide a report or statement of health to an administrator that indicates the compliance of the computer system.

The remediation component 160 can also be part of the agent component 140 or a separate component. The remediation component 140 applies enforcement actions from the rule data store 110 to remediate any violated compliance rules. For example, an enforcement action may specify a set of conditions that are to be met before the system 100 allows a computer system to access the network. If a computer system is non-compliant then the remediation component 160 may, for example, instruct a DHCP client of the computer system not to obtain an IP address for network access or may instruct IPSEC components not to validate the computer system for access to sensitive data on the network.

There are many types of remediation that the flexible compliance system can perform, just a few of which are provided here as examples. Those of ordinary skill in the art will recognize that other types of remediation can easily be plugged into the system described. For example, The computing device on which the system is implemented may include a central processing unit, memory, input devices (e.g., keyboard and pointing devices), output devices (e.g., display devices), and storage devices (e.g., disk drives). The memory and storage devices are computer-readable media that may be encoded with computer-executable instructions that implement the system, which means a computer-readable medium that contains the instructions. In addition, the data structures and message structures may be stored or transmitted via a data transmission medium, such as a signal on a communication link. Various communication links may be used, such as the Internet, a local area network, a wide area network, a point-to-point dial-up connection, a cell phone network, and so on.

Embodiments of the system may be implemented in various operating environments that include personal computers, server computers, handheld or laptop devices, multiprocessor systems, microprocessor-based systems, programmable consumer electronics, digital cameras, network PCs, minicomputers, mainframe computers, distributed computing environments that include any of the above systems or devices, and so on. The computer systems may be cell phones, personal digital assistants, smart phones, personal computers, programmable consumer electronics, digital cameras, and so on.

The system may be described in the general context of computer-executable instructions, such as program modules, executed by one or more computers or other devices. Generally, program modules include routines, programs, objects, components, data structures, and so on that perform particular tasks or implement particular abstract data types. Typically, the functionality of the program modules may be combined or distributed as desired in various embodiments.

In some embodiments, the system signs the statement of health using a cryptographic key. The signature uses a key from the agent deployment component that is deployed with the agent and verifies the authenticity of the statement of health. This allows, for example, the administrator or system to automatically detect when a statement of health has been tampered with and prevents software code already located on the computer system from falsifying a statement of health.

In some embodiments, the network crawl component performs health verification and stores the output. For example, the network crawl component may produce an extensible markup language (XML) file or other report that specifies the compliance rules that a computer system satisfied and/or violated. The agent component consumes the output and performs remediation based on the details of the report.

In some embodiments, the flexible compliance system determines a score for the compliance of a computer system based on the health verification results. For example, some compliance rules may lead to a large score if satisfied (or a large negative score if violated), whereas other rules may have smaller scores. The system uses the score to make a binary system as to whether or not the computer system will be prevented (e.g., quarantined) from accessing the network. A sufficient score indicates that the computer system is far enough out of compliance to pose a risk to the security and health of the network, and thus the system prevents the computer system from accessing the network.

In some embodiments, the agent persists on the computing system after completing an initial verification of the computing system to monitor the compliance of the computer system over time and quarantine the system or provide other remediation as necessary. For example, after logging onto the network a user of the computer system may install a malicious or otherwise non-compliant application or may download a virus that causes the computer system to fall out of compliance. In such cases, the agent may detect the non-compliance condition and remove the computer system from the network. For example, the agent may instruct a TCP/IP stack of the computer system to stop transmitting and receiving packets.

In some embodiments, the flexible compliance system provides provisional access to the network to a computer system that has not yet been verified for compliance. For example, the flexible compliance system may allow the computer system to connect to the network to download the agent, patches, or access other resources. However, if the flexible compliance system determines that the computer system is non-compliant, then the flexible compliance system may limit or remove access to the network from the computer system.

Figure 2:
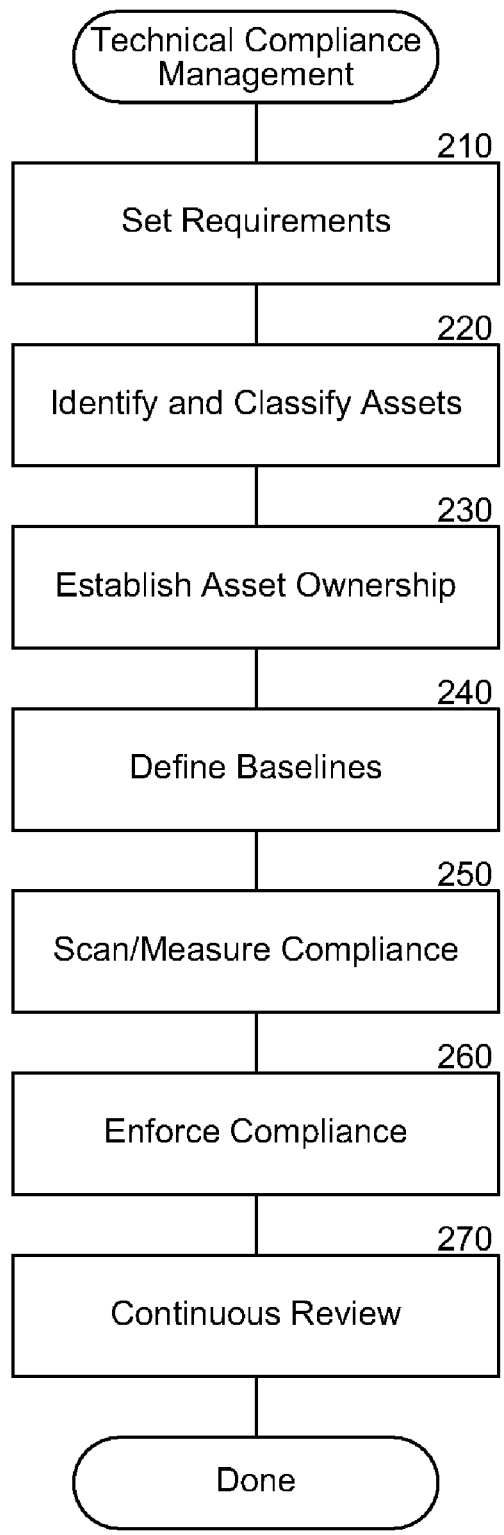
FIG. 2 is a flow diagram that illustrates the steps typically performed by IT personnel in a technical compliance management (TCM) lifecycle including the flexible compliance system, in one embodiment.

FIG. 2 is a flow diagram that illustrates the steps typically performed by IT personnel in a technical compliance management (TCM) lifecycle including the flexible compliance system, in one embodiment. In block 210, IT personnel set requirements. For example, IT personnel may review requirements and obtain executive sponsorship to improve compliance throughout the organization. IT personnel may review policies and standards, consult industry guidelines, begin an asset (e.g., computer systems, network resources, and so on) inventory, and create risk profiles. In block 220, IT personnel identify and classify assets. For example, they may identify systems and business components, determine compliance classifications and groups (e.g., patches, virus signatures, applications), determine compliance metrics, and populate databases related to the TCM lifecycle, such as the rule data store described herein. In block 230, IT personnel establish asset ownership. For example, they may identify stakeholders within the organization, line of business application owners, server and desktop support groups, unmanaged system (e.g., labs) owners, roles and responsibilities, and so forth.

In block 240, IT personnel establish baselines against which to measure compliance. For example, they may identify risk management requirements, security settings, application settings, operating system settings, patch levels, software inventory, and file settings that form the desired compliance level of the organization. In block 250, IT personnel scan and measure compliance, such as using network spider scanners that crawl one or more networks and collect information about various computer systems of the organization. IT personnel may invoke the flexible compliance system to perform this step. This step includes automating technical evaluation (e.g., by generating rules for the flexible compliance system), measuring the effectiveness of compliance controls, reporting compliance, and automating and providing technical triggers for remediation (e.g., by generating remediation steps for the flexible compliance system to perform).

In block 260, IT personnel enforce compliance. For example, they may invoke the flexible compliance system to quarantine computer systems or perform other remediation steps to correct identified compliance problems and restore the health of computer systems within the organization. The flexible compliance system may deploy the lightweight software agent described herein to execute on various computer systems within the organization. In addition, this step may include providing notifications to end users and enforcement systems, forced patching, isolating a system from the network, handling exceptions (e.g., systems that have a legitimate reason for non-compliance), and taking measures to prevent reoccurrences. In block 270, the process repeats in a continues series of reviewing policies and standards, reviewing industry guidelines, updating baseline requirements, re-evaluating the organization's environment, and ensure compliance of computer systems and other resources within the organization.

Figure 3:
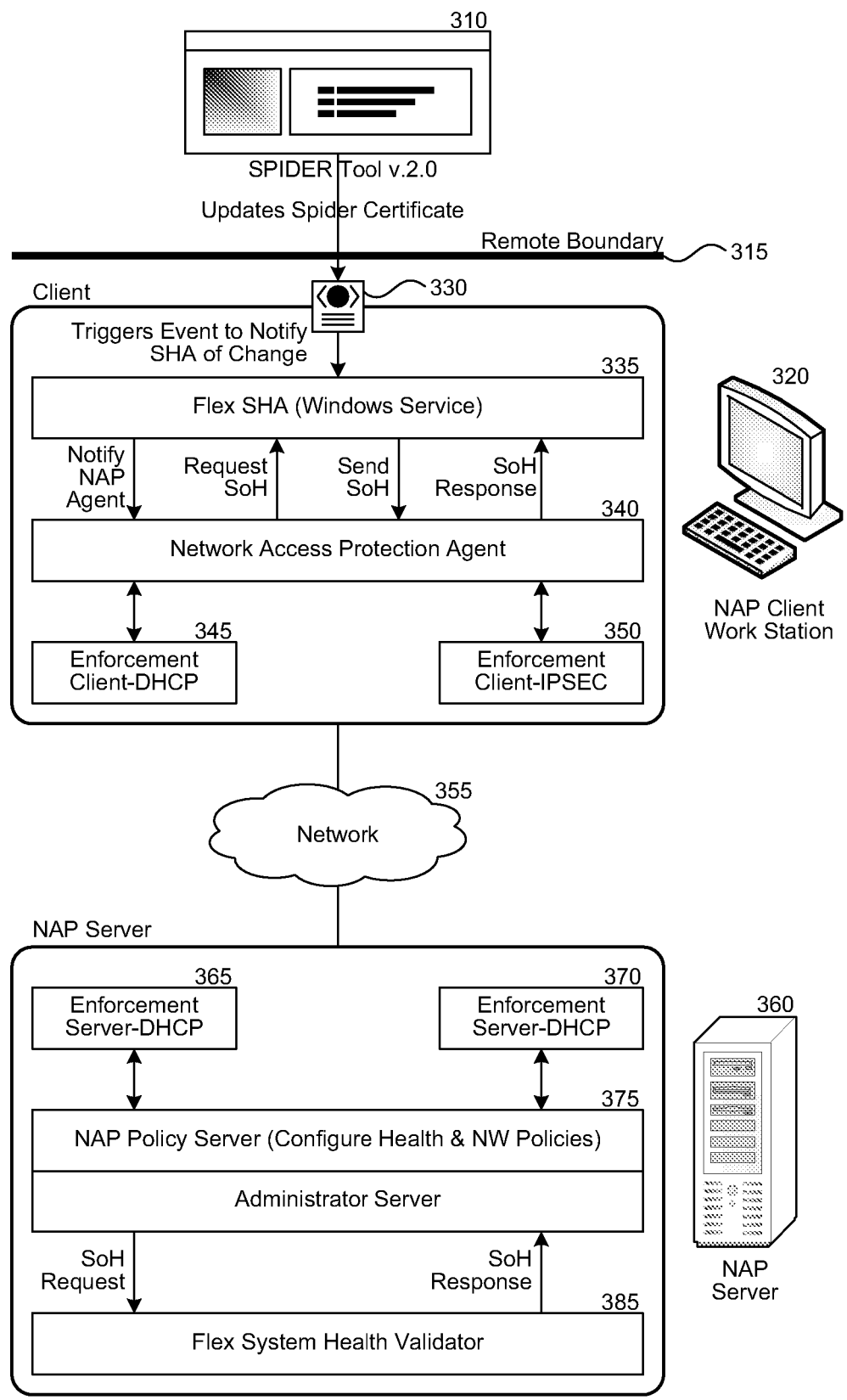
FIG. 3 is a block diagram that illustrates a typical operating environment of the flexible compliance system, in one embodiment.

FIG. 3 is a block diagram that illustrates a typical operating environment of the flexible compliance system, in one embodiment. A spider application 310 assesses the health of various client systems and produces an XML or other document 330 that defines health baselines for a computer system. A client computer system 320 receives the XML document 330. The client computer system 320 contains a flexible system health agent 335, a network access protection agent 340, and one or more enforcement clients, such as a DHCP enforcement client 345 and an IPSEC enforcement client 350. The flexible system health agent 335 notifies the network access protection agent 340 when an event occurs that potentially alters the compliance of the system (e.g., installation of an application) or signals a relevant time to check for compliance (e.g., during logon). The network access protection agent 340 requests a statement of health from the flexible system health agent 335 that indicates the compliance of the client computer system 320 with the policies in the XML document 330. The flexible system health agent 335 assesses the system health, generates the statement of health, and provides it to the network access protection agent 340. If the statement of health is good, indicating that the client system 320 is healthy, then the enforcement clients 345 and 350 allow the client system 320 to connect to the network 355, else the enforcement clients block or restrict access to the network 355.

The operating environment also includes a network access protection server 360 that includes one or more enforcement servers, such as a DHCP enforcement server 365 and an IPSEC enforcement server 370. The enforcement servers determine whether a client computer system 320 can connect to the network. For example, the DHCP enforcement server may not provide an IP address to a client computer system that has not provided a satisfactory statement of health. The enforcement servers interact with a network access protection policy server 375 that stores and enforces the organization's policies. The network access protection policy server 375 may also interact with a flexible system health validator 385 that determines the health of client systems, such as by deploying temporary copies of the flexible system health agent 335 and instructing them to generate a statement of health for a client system.

Figure 4:
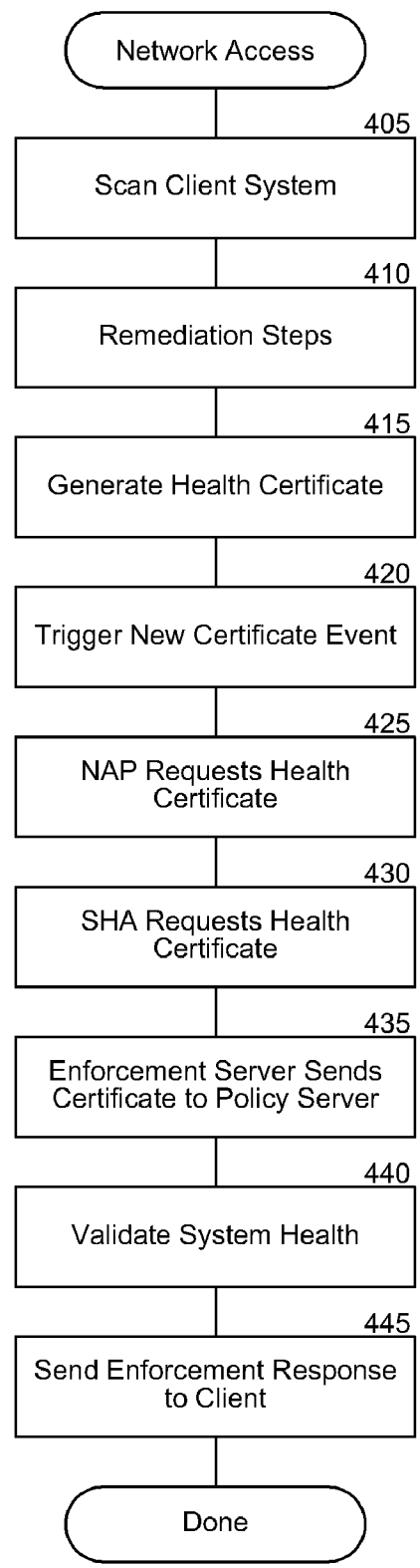
FIG. 4 is a flow diagram that illustrates the interaction between the components of the flexible compliance system to determine whether to grant a client system access to a network, in one embodiment.

FIG. 4 is a flow diagram that illustrates the interaction between the components of the flexible compliance system to determine whether to grant a client system access to a network, in one embodiment. In block 405, a spider engine runs to scan one or more client computer systems. The spider engine may run remotely or locally on each client systems depending on goals of the organization. For example, local scanning can be faster and have less impact on organization resources, but remote scanning can be more secure and less vulnerable to hacking of the client systems. In block 410, the system performs remediation steps based on areas of non-compliance determined by the scan and configurable remediation steps stored in the rule data store. In block 415, the system generates a certificate (e.g., a statement of health) that indicates the health of the client system. The flexible compliance system may store the certificate to keep a historical log of compliance or for other purposes. The certificate may include attributes, such as a pass/fail value that indicates whether the client system should be allowed to access the network and an end time value that indicates the time the scan was completed (e.g., for distinguishing the current scan from subsequent scans).

In block 420, the system triggers a new certificate event and informs the flexible system health agent that a new health certificate is available for the client system. The flexible system health agent then informs the network access protection agent. In block 425, the network access protection agent requests a statement of health from the flexible system health agent and facilitates communication between the flexible system health agent and enforcement client layers. In block 430, the flexible system health agent forwards the request for the statement of health to the network access protection server. The network access protection server has a layer of enforcement server components. Each component is defined for a different type of network access, such as VPN, DHCP, and IPSec. In block 435, an enforcement server component obtains the list of statements of health from the corresponding enforcement client on the client computer system and sends them to a policy server (e.g., using Remote Authentication Dial-In User Service (RADIUS)). In block 440, the policy server communicates with one or more system health validators to validate the client system health based on a configured set of system health policies.

In block 445, the policy server sends an enforcement decision back to the client. For example, if the health of the client is satisfactory, then the policy server sends a response that indicates that the client can access the network. In that case, the enforcement clients permit the client system to access the network. If, on the other hand, the health of the client is not satisfactory, then the response may indicate that the enforcement clients should block the client system from accessing the network. After block 445, these steps conclude.

In some embodiments, the statement of health adheres to a common format with a limited size (e.g., 4,000 bytes) and the flexible compliance system consolidates information to reduce the number of bytes used. For example, whereas previous solutions consume a bit in the statement of health for each compliance test (e.g., antivirus software installed), the flexible compliance system may consume a single bit that provides a pass/fail indication as to whether multiple compliance tests succeeded or failed. The network access protection server does not necessarily know which tests failed or passed, but does know whether the assessment of the client system indicates that the client system should or should not be permitted to connect to the network or other organization resources.

From the foregoing, it will be appreciated that specific embodiments of the flexible compliance system have been described herein for purposes of illustration, but that various modifications may be made without deviating from the spirit and scope of the invention. For example, the system could be used in areas outside of compliance detection and remediation, such as any situation where it is desirable to ensure the state of multiple computer systems. Accordingly, the invention is not limited except as by the appended claims.

I claim:

1. A computer-implemented method for remediating one or more non-compliant computer systems in a network, the method comprising:

receiving one or more compliance rules, wherein the rules include conditions for detecting whether a computer system violates the rule and remediation steps associated with each rule for restoring compliance of the computer system when it violates the rule;

identifying the computer system;

determining the compliance of the computer system with the compliance rules by checking the included conditions;

when the computer system is determined to violate a compliance rule, performing the remediation steps associated with the violated compliance rule on the computer system; and after performing any remediation steps on the computer system, removing the received compliance rules from the computer system.

2. The method of claim 1 wherein the remediation steps include quarantining the computer system from the network.

3. The method of claim 1 wherein the remediation steps include installing an application patch on the computer system.

4. The method of claim 1 wherein identifying the computer system comprises crawling the network with a spider application.

5. The method of claim 1 wherein identifying the computer system comprises receiving a logon notification related to the computer system.

6. The method of claim 1 wherein the received compliance rule conditions identify one or more registry values that indicate compliance of the computer system with the rule.

7. The method of claim 1 wherein the received compliance rule conditions identify one or more file versions that indicate compliance of the computer system with the rule.

8. The method of claim 1 wherein determining the compliance of the computer system comprises iterating through each compliance rule and checking the included conditions for each rule.

9. The method of claim 1 further comprising, when the computer system is determined to violate a compliance rule, determining a severity of the violated compliance rule and performing remediation steps that vary based on the severity.

10. The method of claim 1 further comprising, after determining the compliance of the computer system, generating a statement of health that indicates the compliance of the computer system with the compliance rules.

11. A computer system for maintaining the health of computer systems within an organization, the system comprising:

a rule data store configured to store one or more rules for determining the health of computer systems in an organization;

a network crawl component configured to crawl a network connecting at least some of the computer systems within the organization to identify computer systems the health of which the system maintains;

an agent deployment component configured to deploy a software agent to identified computer systems to execute on the computer systems and to remove the agent from the identified computer systems after remediation is complete; and a flexible agent component configured to report the health of and perform remediation steps on the identified computer systems.

12. The system of claim 11 wherein the flexible agent component further comprises:

a health verification component configured to assess the health of a particular computer system and generate a report of the assessed health; and a remediation component configured to remedy assessed health problems of the computer system.

13. The system of claim 12 wherein the health verification component generates the report as a cryptographically signed statement of health that authenticates the health assessment as having been generated by the flexible agent.

14. The system of claim 11 wherein the rule data store is further configured to store one or more remediation steps used by the remediation component to restore an unhealthy computer system to health.

15. The system of claim 11 wherein the flexible agent component resides temporarily in memory of the computer systems until assessing health and remediation steps are complete.

16. A tangible non-transitory computer-readable medium encoded with instructions for controlling a computer system to automatically provide remediation for compliance problems of the computer system, by a method comprising:

receiving a statement of health that indicates a failure of the computer system to comply with an identified compliance rule;

receiving a script that provides remediation instructions for responding to the failure of the computer system;

automatically performing the instructions of the script to remediate the computer system;

determining that the computer system no longer fails to comply with the identified compliance rule;

updating the statement of health to indicate a current health states of the computer system; and after remediating the computer system, removing the received script from the computer system.

17. The tangible non-transitory computer-readable medium of claim 16 wherein the remediation instructions provide instructions for restoring the compliance of the computer system with the identified compliance rule.

18. The tangible non-transitory computer-readable medium of claim 16 wherein the remediation instructions provide instructions for quarantining the computer system from other computer systems on a network.

19. The tangible non-transitory computer-readable medium of claim 16 wherein the script is received as an XML file that specifies one or more rule conditions for detecting compliance with the compliance rule and remediation instructions associated with the compliance rule.

20. The tangible non-transitory computer-readable medium of claim 16 wherein the remediation instructions include at least one of modifying a registry key, deleting a file, and uninstalling an application.

* * * * *